United States Patent

Koskan et al.

[11] Patent Number: 5,861,356
[45] Date of Patent: Jan. 19, 1999

[54] METHOD AND COMPOSITION FOR ENHANCED PLANT PRODUCTIVITY COMPRISING FERTILIZER AND CROSS-LINKED POLYAMINO ACID

[75] Inventors: Larry P. Koskan, Orland Park; Abdul Rehman Y. Meah, Justice; J. Larry Sanders, Lockport; Robert J. Ross, Elmhurst, all of Ill.

[73] Assignee: Donlar Corporation, Bedford Park, Ill.

[21] Appl. No.: 778,147

[22] Filed: Jan. 10, 1997

Related U.S. Application Data

[63] Continuation-in-part of Ser. No. 313,436, Sep. 27, 1994, Pat. No. 5,593,947, which is a continuation-in-part of Ser. No. 972,375, Nov. 5, 1992, Pat. No. 5,350,735.

[51] Int. Cl.$^6$ .............................. A01N 37/18; C05G 3/00
[52] U.S. Cl. ..................... 504/149; 504/283; 504/320; 504/335
[58] Field of Search ................................ 504/149, 283, 504/320, 335

[56] References Cited

U.S. PATENT DOCUMENTS

| | | | |
|---|---|---|---|
| 4,590,260 | 5/1986 | Harada et al. | 528/328 |
| 4,839,461 | 6/1989 | Boehmke | 528/363 |

*Primary Examiner*—S. Mark Clardy
*Attorney, Agent, or Firm*—Olson & Hierl, Ltd.

[57] ABSTRACT

This invention relates to enhancing plant productivity employing a method and improved compositions containing water-soluble crosslinked polyamino acids having a weight average molecular weight of a size larger than about 1,500. More particularly, crosslinked polyamino acids enhance plant productivity when supplied to the plant directly as the free acid or salt thereof or hydrolyzed from a crosslinked precursor of the crosslinked polyamino acid by the method disclosed. Particularly suitable for this purpose are water-soluble, crosslinked polyaspartic acid, and salts thereof and hydrolyzed crosslinked polysuccinimide.

33 Claims, 3 Drawing Sheets

CONTROL  
FULL FERTILIZER

DGI - K1 - (10ppm)  
FULL FERTILIZER

CONTROL  
FULL FERTILIZER

DGI - K1 - (10ppm)  
1/3 FERTILIZER

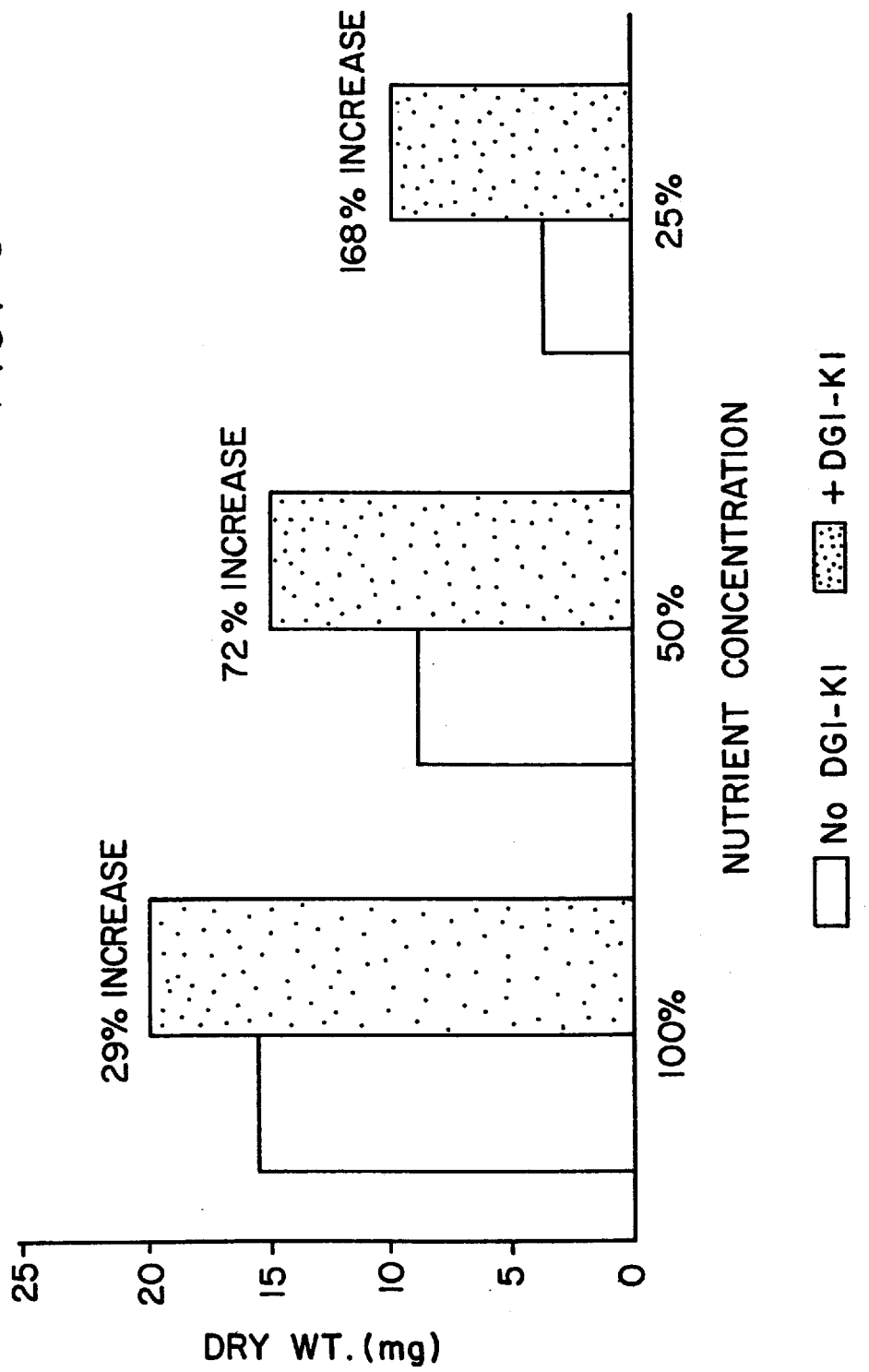

METHOD AND COMPOSITION FOR ENHANCED PLANT PRODUCTIVITY COMPRISING FERTILIZER AND CROSS-LINKED POLYAMINO ACID

CROSS-REFERENCE TO RELATED APPLICATION

This application is a continuation-in-part of U.S. Ser. No. 08/313,436, filed on Sep. 27, 1994, now U.S. Pat. No. 5,593,947, which is a continuation-in-part of U.S. Ser. No. 07/972,375, filed on Nov. 5, 1992, now U.S. Pat. No. 5,350,735.

TECHNICAL FIELD

This invention relates to a method and composition for enhancing the productivity of plants. More particularly, this invention relates to absorption phenomena that facilitate the assimilation and utilization of nutrients by plants through either seed, root or foliar pathways.

BACKGROUND OF THE INVENTION

Organic acids and oligomers thereof have been shown to promote plant growth. Typical promoters of plant growth are described by Kinnersley et al., *Plant Growth Regulation*, 9, pp. 137–146 (1990) (lactic acid and relatively low molecular weight oligomers of lactic acid); in U.S. Pat. No. 4,813,997 to Kinnersley et al. (oligomers of glycolic and/or L-lactic acid) and in U.S. Pat. No. 4,799,953 to Danzig et al. (oligomers of thiolactic and thioglycolic acids). All of the forgoing approaches to plant growth promotion appear to focus on coordination as a means for increasing plant uptake of compounds vital to the growth of the plant, e.g., micronutrients such as calcium, magnesium, sulfur, manganese, zinc, copper, iron, boron, and the like.

A common approach to promoting plant growth has been, and continues to be, the use of nutrients (fertilizers), natural as well as synthetic. Synthetic nutrients usually provide nitrogen in a plant-usable form, such as urea for example, and/or inorganic nitrates, phosphates, or the like compounds. While such nutrients may be applied, more or less, at the convenience of the farmer, and may be applied as often as deemed desirable, the overuse of synthetic nutrients and the inefficient use of synthetic nutrients are major factors responsible for environmental problems such as eutrophication of groundwater, nitrate pollution, phosphate pollution, and the like. An overview of the undesirable effects of nitrogen fertilizer is presented by Byrnes, *Fertilizer Research*, 26, pp. 209–215 (1990).

To ameliorate the problems attendant to inefficient nutrient use and nutrient overuse, there is an ongoing desire and need for environmental and production reasons to increase fertilizer efficiency and enhance plant productivity. There is a need, therefore, to maximize the availability, uptake and utilization of plant nutrients while minimizing loss of nutrients or fertilizer elements through leaching, denitrification, vaporization and other mechanisms that prevent assimilation of these nutrients by the biological and physical mechanisms of plants.

The present invention addresses and resolves these problems by methods and compositions which provide a favorable environment for enhancing the utilization of nutrients by germinating or growing plants resulting in enhanced plant productivity.

SUMMARY OF THE INVENTION

The present invention provides a method and improved compositions for enhanced plant productivity by achieving more efficient utilization of nutrients.

The present method comprises supplying to a plant a composition containing a productivity enhancing amount of a water-soluble, crosslinked polyamino acid having a weight average molecular weight (Mw) such that it is not absorbed by the plant, i.e., larger than about 1,500. The crosslinked polyamino acid can be supplied in the form of the free acid or salt thereof or can be hydrolyzed from a precursor thereof which is water soluble and has a weight average molecular weight (Mw) larger than about 1,500. The method as practiced provides a more favorable environment for assimilation and utilization of nutrients by the plant, via its seed, root feeding zone, foliar mechanisms for absorption and translocation, growth medium or combinations thereof.

The crosslinked polyamino acid can be supplied to the plant directly or as a crosslinked precursor of polyamino acid which can hydrolyze in situ in an alkaline moist or wet environment to a crosslinked polyamino acid. Particularly preferred is water-soluble crosslinked polyaspartic acid and salts thereof and its precursor, crosslinked polysuccinimide. The crosslinked polyamino acid or salt thereof can be supplied separately or in combination with fertilizer.

Preferred crosslinked polyaspartic acid is prepared from polyaspartic acid having aspartic acid residues of at least 20% of the total number of residues in the polymer. Crosslinked polyaspartic acids preferably have, prior to crosslinking, at least 15 repeating amino acid units or mers in the polymer chain.

The crosslinked polyamino acids also can be used in combination with uncrosslinked polyamino acids and water-soluble, non-peptidal polymers.

The method and compositions of this invention beneficially provide stress protection to plants and promote growth in environments containing salts present in concentrations that are normally toxic to plants. Further, a more favorable environment is provided which supplies the nutritional elemental requirements to the plant employing nutritional levels that are lower than are required with conventional fertilizers.

BRIEF DESCRIPTION OF THE DRAWINGS

In the drawings, there are shown photographic reproductions of corn plants treated in a particular manner alongside a control corn plant. In each case a yardstick (36 inches) is shown positioned between the photographed plants to indicate scale. In particular.

FIG. 5 is a graphical representation of growth enhancement with polyaspartic acid.

DETAILED DESCRIPTION OF PREFERRED EMBODIMENTS

Figure 1:
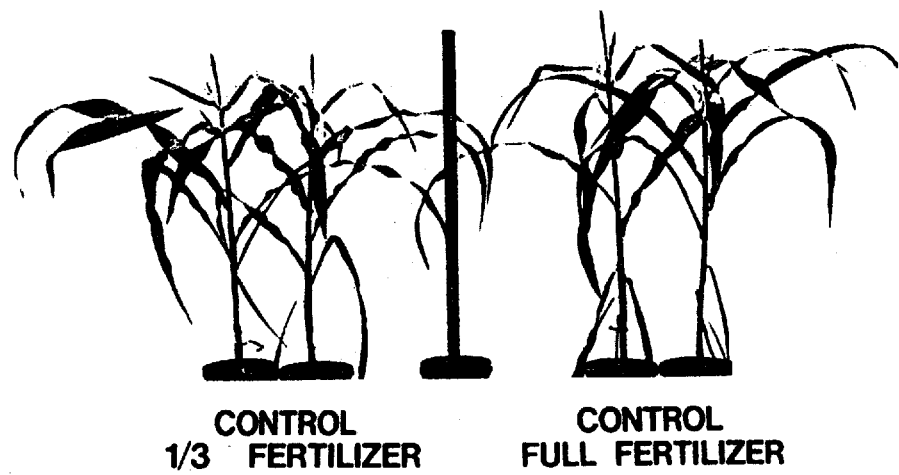
FIG. 1 shows corn plants 40 days after planting, and treated with one-third of the recommended fertilizer dosage alongside a corn plant treated with the recommended dosage for the same fertilizer.
Figure 2:
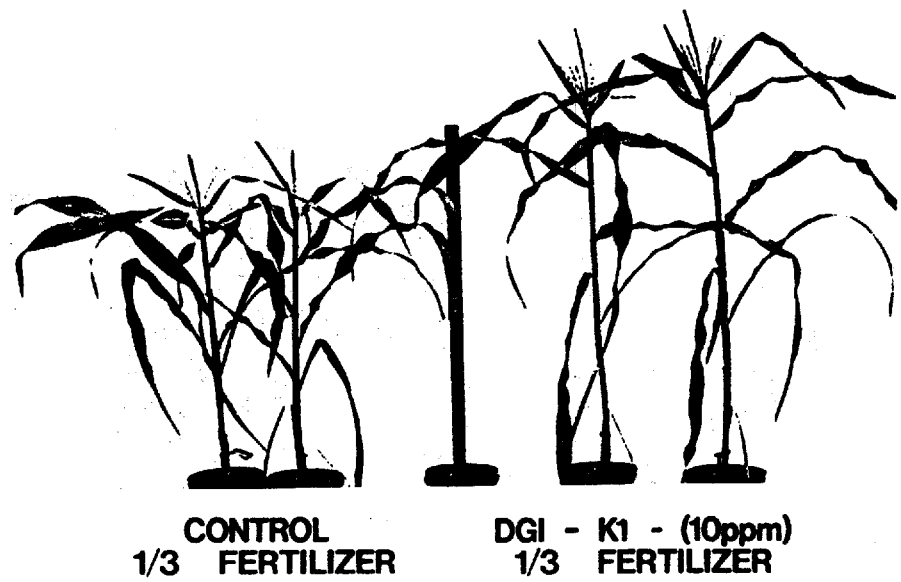
FIG. 2 shows a corn plant 40 days after planting, one treated with one third of the recommended fertilizer dosage alongside a corn plant similarly treated with the same fertilizer but also with 10 parts per million by weight of polyaspartic acid.

The present invention is directed to a method and improved compositions for enhancing plant productivity.

Enhanced plant productivity is achieved by making nutrients more readily available to the plant through its seed, root feeding zone, foliar absorption and translocation mechanisms, its growth medium or combinations thereof. Thus a more favorable environment is provided for increased assimilation and efficient utilization of applied natural or chemical nutrients by plants.

The present invention in its various aspects, is predicated, in part, on the discovery that polymeric acids, and polymeric amino acids in particular, of a molecular size too large to enter a plant nevertheless can provide a favorable environment for enhanced plant productivity. The more efficient utilization of nutrients can be realized in the presence of the polymeric acid inasmuch as relatively lower nutrient dosages can be relied upon to provide the requisite nutrients to the plant.

The term "enhanced plant productivity" as used herein means that at least one or more of the following factors is achieved: increased growth rate, increased biomass, higher yields and quality (i.e., increased protein content), accelerated rate of root formation, increased tillering, increased chlorophyll concentration and the like indicia.

The term "crosslinked polyamino acid" as used herein includes water-soluble salts of the crosslinked polyamino acid. Preferred crosslinked polymeric amino acids of the present invention may contain aspartic acid monomer units linked by alpha peptide bonds, beta peptide bonds or both and/or glutamic acid monomer units linked by alpha peptide bonds, gamma peptide bonds or both.

The term "crosslinked polysuccinimide" as used herein refers to substantially water-soluble random copolymers comprised of succinimide units and structural units derived from a monomeric crosslinking agent. Crosslinked polysuccinimide preferably contains substantially no alpha-aspartate and beta-aspartate units or a relatively small proportion thereof such that the combined amount of alpha-aspartate and beta-aspartate units is less than about 20% of the polymer. The amount of crosslinking is limited to the extent that crosslinking does not materially affect the solubility of the crosslinked polyaspartic acid produced when crosslinked polysuccinimide is subsequently hydrolyzed in an alkaline aqueous medium.

More particularly, the present invention is directed to employing a productivity enhancing amount of crosslinked polyamino acid or hydrolyzable crosslinked precursor thereof. The degree to which the polyamino acid is crosslinked is limited only to the extent that crosslinking does not materially affect the solubility of the crosslinked polymer moiety in polar solvents, such as water, alcohol or mixture thereof.

A preferred polyamino acid in crosslinked or uncrosslinked form which is well suited for the practice of this invention to provide more efficient utilization of both natural and synthetic plant nutrients is polyaspartic acid. This polymer can be conveniently prepared from L-aspartic acid, D-aspartic acid or DL-aspartic acid, or from aspartic acid precursors (ammonium maleate, maleamic acid, ammonium malate, diammonium maleate, diammonium malate, ammonium maleamate, ammonium fumarate, diammonium fumarate) using thermal condensation methods.

Crosslinked polyamino acids are preferably water soluble and produced from polyaspartic acid moieties containing aspartic acid monomer units linked by α peptide and β peptide bonds and structural units derived from a monomeric crosslinking agent.

Useful crosslinked polyaspartic acids are random copolymers structurally comprised of monomer units of succinimide (structural formula S), alpha-aspartate (structural formula A), beta-aspartate (structural formula B) and crosslinking dimeric aspartamides (structural formula having any one of the following three structural formulas, $L^1$, $L^2$ and $L^3$), trimeric aspartamides (having the structural formula $L^4$) or tetrameric aspartamides (having the structural formula $L^5$). For convenience, these will be referred to collectively as structural formula (L).

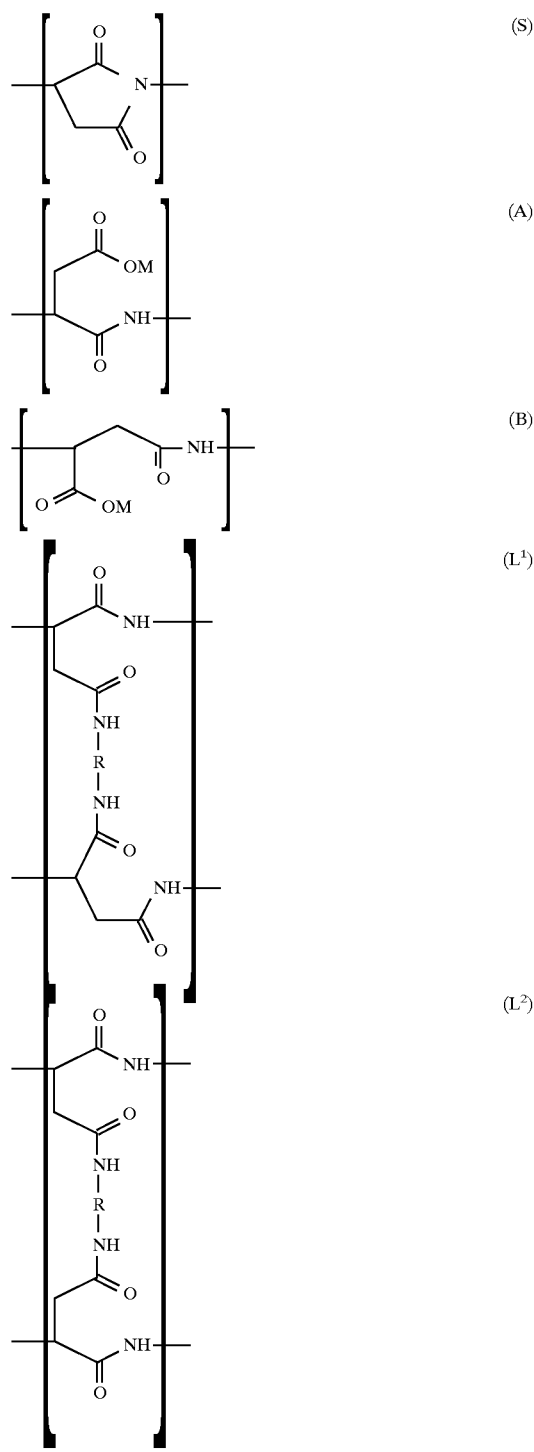

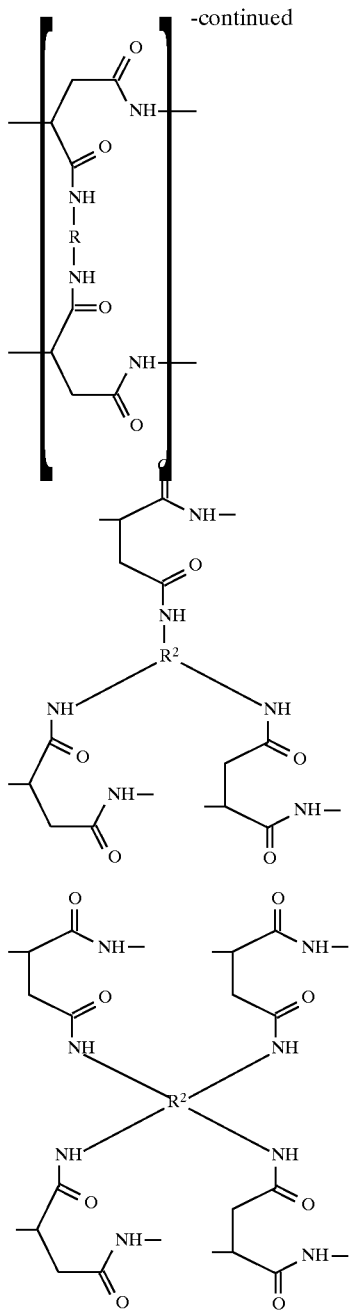

In the structural units, (A) and (B), M can be a hydrogen ion, an alkali metal cation such as Na$^+$, K$^+$ or Li$^+$, an ammonium ion, or quaternary ammonium ion. The term "crosslinked polyaspartic acid" and its various grammatical variations as used herein includes water-soluble salts of crosslinked polyaspartic acid.

In the structural (L) units, (L$^1$), (L$^2$) and (L$^3$), R is a divalent organic linking group derived from an organic crosslinking agent, preferably containing 1 to about 20 carbon atoms and optionally aliphatic and/or aromatic ring structures. The organic crosslinking agent preferably is an organic base containing at least two primary amine groups capable of reacting with a succinimide monomer unit to form a crosslink thereof, for example, aliphatic diamines, such as ethylene diamine (EDA), 1,3-bis(aminoethyl) cyclohexane (1,3-BAC), and hexamethylene diamine (HMDA); arylaliphatic diamines, such as meta-xylylenediamine (MXDA); and polyether diamines, such as polyoxyalkylene diamines and amine terminated block copolymers of polyoxyalkylene/polyalkylene glycols, amine terminated polypropylene glycols having an average of from about 2 to about 68 propylene oxide units, amine terminated polyethylene/polypropylene glycols, triethylene glycol diamine and tetraethylene glycol diamine, amine terminated polyalkyleneimines, such as diethylene triamine (DETA) and tetraethylene pentamine (TEPA).

In the respective structural formula (L) units, (L$^4$) and (L$^5$), R$^2$ is a trivalent and tetravalent organic linking group derived from triamino, tetraamino and polyamino crosslinking agents, such as tris(2-aminoethyl)amine (TAEA), polyamines and propylene oxide based triamines varying in molecular weight from about 440 to about 5,000 and polyvinylamine polymers.

For convenience, reference to the term "(L) units" includes any one of the monomeric crosslinking (L) structural units without limitation.

The terms "crosslinked polyaspartate" or "crosslinked polyaspartic acid" are used interchangeably herein to refer to such water-soluble random copolymers structurally comprised primarily of (A), (B) and (L) units having a weight average molecular weight (Mw) larger than about 1,500, more preferably of at least about 2,000. Crosslinked polyaspartates preferably contain no (S) units or relatively small proportions of less than about 20%.

Counterions for polyaspartates include, but are not limited to, the alkali metal ions, preferably Na$^+$, K$^+$, and Li$^+$; alkali earth metal cations, preferably Mg$^{++}$, Ca$^{++}$ and Ba$^{++}$; transitional metal ions, preferably Zn$^{++}$, Co$^{++}$, Fe$^{++}$ and Fe$^{+++}$ and NH$_4^+$.

Water-soluble crosslinked polyaspartic acid and crosslinked polysuccinimide useful as hydrolyzable precursors can be synthesized by any method. For example, preferred soluble crosslinked polyaspartates and crosslinked polysuccinimides of varying Mw can be produced by the method described in U.S. Pat. No. 5,552,516 to Ross et al., incorporated herein by reference, or can be produced by well known free radical crosslinking techniques. Presently preferred, but not limited thereto, are the sodium salt of polyaspartic acid crosslinked with 10 mol % metaxylylenediamine, preferably having a Mw of about 80,000 and the sodium salt of a copolymer of 80 mol % aspartic acid/20 mol % N-allylaspartamide free radical crosslinked with hypophosphite, preferably having a Mw of about 53,311.

The crosslinked polyamino acids can also be used in combination with water-soluble uncrosslinked polyamino acids, such as polyaspartic acid, polyglutamic acid, polysuccinimide, polylactic acid, polyglycolic acid and mixtures thereof.

Polysuccinimide and polyaspartic acids useful, directly or in crosslinked form, in this invention are represented by the following structures:

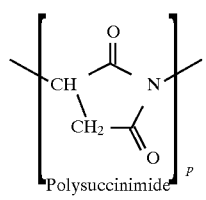

-continued

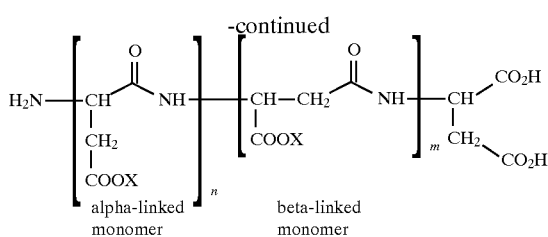

alpha-linked monomer    beta-linked monomer where X=$H^+$, $Na^+$, $NH_4^+$, $K^+$, $Ca^{++}$, $Mg^+$, $Zn^{++}$, $Co^{++}$, $Li^+$, $Ba^{++}$, $Fe^{++}$, $Fe^{+++}$ and the value of the integers n, m and p are such that the copolymer and polymer, if present, has a weight average molecular weight larger than about 1,500 daltons.

The polyaspartic acid moieties contain aspartic acid monomer units linked by α peptide and β peptide bonds. A preferred polyaspartic acid is β-polyaspartic acid, i.e., one having >50 mole % of aspartic acid units linked by β peptide bonds and <50 mole % of aspartic acid units linked by α peptide bonds. Preferably, 60–80 mole % of the polyaspartic acid is in β-linkage form and the polyaspartic acid has a Mw within the range of 2,000–100,000. More preferably, approximately 70 mole % to 80 mole % of the polyaspartic acid has β form and has a Mw within the range of 2000–20,000. Most preferably, approximately 70 mole % to 75 mole % of the polyaspartic acid has β form and 25 mole % to 30 mole % α, and has a Mw within the range of 2000–5000.

A preferred polyaspartic acid moiety is β-polyaspartic acid, i.e., one having >50 mole % of aspartic acid units linked by β peptide bonds and <50 mole % of aspartic acid units linked by α peptide bonds. Preferably, 60–80 mole % of the polyaspartic acid moiety is in β-linkage form and the polyaspartic acid moiety has a Mw within the range of about 2,000 to about 100,000. More preferably, approximately 70 mole % to 80 mole % of the polyaspartic acid moiety has β form and has a Mw within the range of about 2,000 and about 20,000. Most preferably, approximately 70 mole % to 75 mole % of the polyaspartic acid moiety has β form and 25 mole % to 30 mole % α form, and has a Mw within the range of 2,000–5,000.

In general, the water soluble but crosslinked polymeric amino acids can be made available to the plant in the form of aqueous liquids or in substantially solid form and supplied to the plant by any convenient manner of application.

Preferably, aqueous nutrient solutions supplied to the plant contain at least about 10 parts per billion (ppb) by weight, preferably about 0.1 to about 1,000 parts per million (ppm) by weight, more preferably about 1 to about 500 ppm by weight, of the crosslinked polymeric amino acid with or without uncrosslinked polymeric amino acid present in the solution. Such solutions can be applied to the soil surrounding the plant so as to contact the plant's root system, can be applied to the plant's foliage utilizing usual foliar feeding techniques, can be introduced into hydroponic gardening or farming systems, and in any other convenient manner. For example, such solutions can be sprayed or otherwise applied to contact the roots, stems, or leaves of the plants whose productivity, growth and/or development is to be enhanced, as well as to the seeds or reproductive parts of these plants, in an amount as is discussed in greater detail hereinbelow.

Aqueous nutrient solutions containing the crosslinked polymeric amino acid, preferably derived from polyaspartic acid, are also useful to enhance effective plant productivity under stressful growth limiting conditions, e.g., in soil that contains salts or metal ions in concentrations normally toxic to plants, soil depleted in certain nutrients, etc.

The crosslinked polymeric amino acids, with or without uncrosslinked polyamino acid, preferably derived from polyaspartic acid, can also be applied to soil in substantially solid form alone or in combination with nutrients. For example, granular, pelletized, dust or powdered forms of the crosslinked polyamino acids can be applied by gravity or air blast equipment into the furrow, row or site at seeding or planting time. Dry granular or pelleted forms of the crosslinked polyamino acids, preferably derived from polyaspartic acid, can be impregnated or pre-formed as carriers of nutrients and can then be used for surface application by ground rig or aircraft.

The crosslinked polymeric amino acids, like uncrosslinked polymeric amino acids, can be supplied to the plant as a precursor in an anhydrous form, as for example crosslinked polysuccinimide (preferably derived from anhydropolyaspartic acid). In combination with a basic material in the presence of water, soil moisture, rainfall, etc. such precursors can hydrolyze in situ to crosslinked polyaspartic acid and salts thereof. Basic materials which can be used are sodium carbonate, sodium bicarbonate, limestone, ammonia and the like. Crosslinked polysuccinimide can be applied and mixed with the solid basic material in powder, pellet or granule form or can be incorporated into an aqueous growth medium, such as a hydroponic medium, preferably under alkaline conditions.

For example, crosslinked polysuccinimide can be mixed with sodium carbonate or sodium bicarbonate and applied as a powder, as a dry granule or in pellet form. The sodium carbonate and sodium bicarbonate will hydrolyze crosslinked polysuccinimide to crosslinked polyaspartic acid sodium salt in moist or wet soil. Crosslinked polysuccinimide can also be applied to soil as a powder, pellet or as granules mixed with limestone (Ca and Mg carbonate). In this application, the carbonates of the limestone can hydrolyze the crosslinked polysuccinimide to crosslinked polyaspartic acid sodium salt in moist or wet soil. Another way of using crosslinked polysuccinimide is to apply it to soil as a powder, granule or pellet after the soil has received an injection of ammonia. In this process, ammonium hydroxide formed from the ammonia and water in the soil will hydrolyze the crosslinked polysuccinimide to crosslinked polyaspartic acid.

The polymeric amino acids from which crosslinked polymeric amino acids can be produced, to be suitable for the practice of the present invention, must be or become water soluble, and have a molecular size sufficiently large to preclude absorption into the plant's own system. To that end, the polymeric amino acids and crosslinked polymeric amino acids deemed suitable for the present purposes, while hydrophilic, have a Mw larger than about 1,500 and have at least about 15 repeating amino acid units (residues), or mers, in the linear polymer chain that constitutes the polymeric amino acid prior to crosslinking. Suitable linear polymer chains are crosslinked to a degree that does not materially affect the water solubility of the resulting crosslinked polymeric moiety.

Polymeric amino acids having a molecular size in excess of about 100,000 Mw usually do not exhibit adequate solubility in water for the present purposes. Thus a polymeric amino acid or crosslinked polymeric amino acid of a molecular size not larger than about 100,000 Mw is presently preferred. A useful molecular size is in the range of about 1,500 to about 85,000 Mw, preferably in the range of about 1,600 to about 85,000 Mw, more preferably in the range of about 1,700 to about 60,000, most prefereably in the range of about 2,000 to about 30,000 Mw.

Illustrative useful polymeric amino acids from which crosslinked polymeric amino acid can be produced include, but are not limited to, those having side chains containing carboxylic acid, thiocarboxylic acid, mercapto, hydroxy, imidocarboxy, and/or amino moieties. Preferred such polymeric amino acids or salts thereof can be selected from the group consisting of polyaspartic acid, polyglutamic acid, polylysine, polyglycine, polycysteine, polyserine, copolymers thereof, such as polycysteine/glutamic acid and terpolymers thereof, such as polycysteine/glutamic/aspartic acid. Also useful are block or random copolymers or terpolymers of polyamino acids and non-amino organic acids, such as a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, mixtures of the foregoing, and the like.

Also useful is polysuccinimide supplied directly or in water-soluble crosslinked form or a copolymer containing succinimide residues and partially hydrolyzed polysuccinimide which can be hydrolyzed in situ to polyaspartic acid, crosslinked polyaspartic acid or mixtures thereof.

The polymeric amino acids and crosslinked polymeric amino acids of this invention can be used in combination with water-soluble, non-peptidal polymers to provide more efficient utilization of both natural and synthetic plant growth nutrients.

Examples of water-soluble, non-peptidal polymers which can be used include, but are not limited to, water-soluble, non-peptical polycarboxylates, such as polylactic acid, polyglycolic acid, polyacrylic acid, polymaleic acid, polyitaconic acid, and polymethacrylic acid, polyacrylamide and copolymers thereof such as, but not limited to, acrylamide-acrylic acid copolymers, acrylamide/2-acrylamido-2-methylpropanesulfonic acid copolymers, acrylamide/diallyldimethylammonium chloride copolymers, acrylamide/dimethylaminoethyl methacrylate and acrylate copolymers and methyl chloride or sulfate quaternized derivatives of these copolymers, acrylic acid/maleic acid copolymers, acrylic acid/itaconic acid copolymers, maleic acid/itaconic acid copolymers, methacrylic acid/acrylamide copolymers, methacrylic acid/acrylic acid copolymers polyvinyl alcohols and polyvinylpyrrolidone.

The water-soluble, non-peptidal polymers which can be used in combination with the polyamino acids and crosslinked polyamino acids should have a molecular size larger than about 1,500 Mw and preferably have at least about 15 repeating monomer units, or mers, in the linear polymer chain that constitutes the water-soluble polymer. For present purposes, a water-soluble polymer of molecular size not larger than about 100,000 Mw is preferred.

Polymeric amino acids suitable for use in the present invention can be made, inter alia, by thermal condensation methods. See, for example, U.S. Pat. No. 5,057,597 to Koskan; U.S. Pat. No. 5,221,733 to Koskan et al.; U.S. Pat. No. 5,219,952 to Koskan et al.; Little et al., *American Chemical Society*, 97, 263–279 (1991) and U.S. Pat. No. 4,696,981 to Harada et al.

The starting materials for the polymerization, i.e., the amino acid monomers, can exist as optical isomers and can be polymerized either as a racemic mixture or as segregated optical isomers.

Particularly well suited for the practice of the present invention, and from which crosslinked polyamino acids can be prepared, are the polyamino acids such as polyaspartic acid having a Mw in the range of about 3,000 to about 100,000, polyglutamic acid having a Mw in the range of about 4,000 to about 14,000, polyglycine having a Mw in the range of about 1,500 to about 7,000, and polylysine having a Mw in the range of about 2,000 to about 7,000.

The aforesaid polyamino acids and crosslinked polyamino acids thereof increase the efficiency of utilization of nutrients, both natural and synthetic. The nutrients can be those found naturally in the soil or plant growth medium or can be those which are added or can be those that are residual nutrients from previous nutrient treatments. More efficient utilization by the growing plants of both macronutrients, such as but not limited to, nitrogen (N), phosphorus (P), potassium (K) and micronutrients, such as but not limited to, calcium (Ca), magnesium (Mg), sulfur (S), zinc (Zn), iron (Fe), manganese (Mn), boron (B), cobalt (Co), molybdenum (Mo), copper (Cu) and nickel (Ni) is accomplished by employing the polyamino acids and crosslinked polyamino acids of this invention.

There are many uses and applications for the present inventions in its various aspects. Illustrative are uses in agriculture, gardening, horticulture, hydroponics, forestry, land reclamation (e.g., landfills, soils with relatively high salt concentrations, etc.), and the like.

Suitable dosage rates of crosslinked or uncrosslinked polymeric amino acid component of the present invention, so as to provide a sufficient productivity enhancing amount of crosslinked or uncrosslinked polymeric amino acid to the plant to enhance nutrient utilization by the plant can be about two to about 500 ounces of the crosslinked or uncrosslinked polymeric amino acid per acre. Crops with an abundance of foliage, such as wood crops, grain crops, cotton, etc., usually are treated at dosage rates in an intermediate range, i.e., about 25 to about 250 ounces per acre. Relatively lower dosage rates within the foregoing overall range, i.e., about two to about 25 ounces per acre, usually are sufficient for agricultural row crops, flowering nursery crops, and the like.

The polymeric amino acid or crosslinked polymeric amino acid can be made available to the plant as a separate treatment, or in combination with water-soluble, non-peptidal polymers and/or in combination with nutrients (fertilizers). Substantially solid as well as liquid dosage forms can be utilized for this purpose, e.g., aqueous solutions, solid soil conditioning substances such as particulate clays bearing the polymeric amino acid commingled with nutrient components, solid particulate admixtures of polymeric amino acid, nutrient and the like.

The present invention is further illustrated by the following examples which demonstrate more efficient utilization of plant growth nutrients.

EXAMPLE 1

More Efficient Usage of Nutrients in Corn Plants

White corn (Early Sunglow; George W. Park Seed Co., Greenwood, S.C.) was grown in a greenhouse in one gallon pots filled with Fafard 3B potting soil. To each pot was added Peters™ 20-20-20 fertilizer in an amount representing a full dose of nutrients or a ⅓ dose of nutrients. A portion of the pots so treated also received an aqueous solution of polyaspartic acid (PA) (50 ml; 10 ppm by weight of PA having a weight average molecular weight (Mw) of about 3,000–5,000. The growth rates of the white corn plants in these pots were monitored, and representative plants were photographed 40 days after planting. These photographs are depicted in FIGS. 1 through 4.

Figure 3:
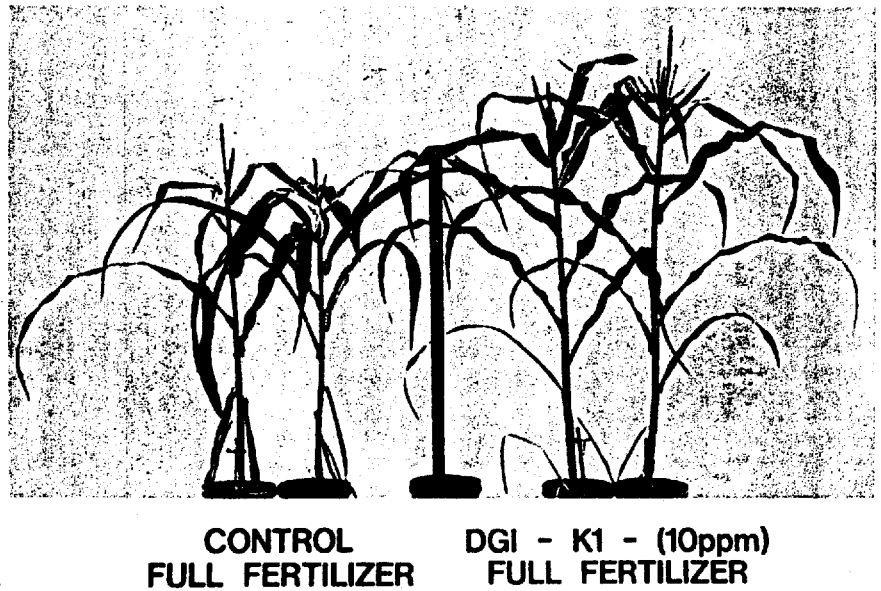
FIG. 3 shows corn plants 40 days after planting, both treated with the recommended fertilizer dosage and one plant also with 10 parts per million by weight of polyaspartic acid.
Figure 4:
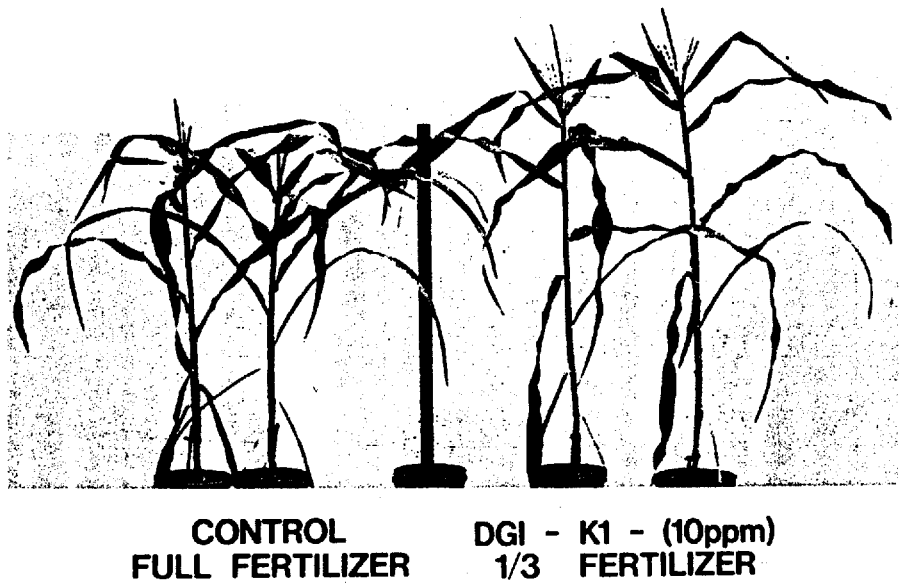
FIG. 4 shows corn plants 40 days after planting, one treated with the recommended fertilizer dosage and the other with one-third of the recommended fertilizer dosage but also with 10 parts per million by weight of polyaspartic acid.

These Figures show that the availability of PA to the plant enhanced plant growth at a reduced nutrient level, i.e., corn plants treated at one-third of the nutrient level but with 10 ppm of PA added (FIG. 4) show greater growth than corn plants will the full amount of nutrient. Corn plants grown using the full nutrient level also undergo enhanced growth when 10 ppm of polyaspartic acid is used along with the nutrient (FIG. 3). Both tests demonstrate a more efficient utilization of nutrients for plant growth.

EXAMPLE 2

Effects of Polyaspartic Acid on Growth Patterns of Corn Plants with No Added Fertilizer White corn (Early Sunglow; George W. Park Seed Co., Greenwood, S.C.) was grown in a greenhouse in one gallon pots filled with Fafard 3B potting soil. No fertilizer was added to each pot. A portion of the pots so treated received aqueous solutions of polyaspartic acid (PA) of varying dosage levels (50 ml of solution; 1 ppm, 10 ppm, 100 ppm, and 1,000 ppm of PA having a Mw of about 3,000–5,000. The growth rates of the white corn plants in these pots were monitored on a weekly basis and the data is shown in Table I, below.

TABLE I

GROWTH PATTERNS OF EARLY SUNGLOW CORN; NO ADDED FERTILIZER; SINGLE TREATMENT

| Dosages of PA | Height Change (inches) | | | |
| --- | --- | --- | --- | --- |
| | Week 1 | Week 2 | Week 3 | Week 4 |
| Control (No PA) | 13.0 | 9.0 | 6.4 | 5.2 |
| 1 ppm | 12.5 | 9.4 | 5.4 | 5.7 |
| 10 ppm | 11.6 | 11.0 | 5.0 | 7.0 |
| 100 ppm | 11.4 | 10.4 | 6.4 | 7.2 |
| 1000 ppm | 10.4 | 10.4 | 5.6 | 7.8 |

The data shown in Table I indicates that after one week of growth, corn plants with no added fertilizers but with PA added in dosages of 1 to 1,000 ppm received no benefit from PA treatment. After week 2 of corn plant growth, a beneficial effect was shown at all four dosage levels of PA. After three weeks of growth, only the 100 ppm dosage level of PA showed a benefit over no PA treatment. Finally after four weeks of corn plant growth, a low level of plant growth was occurring but increased growth rate was observed with all four dosage levels of PA. In summary, during the initial stage (first week) of corn plant growth PA did not increase growth rate without added fertilizer. However, after the next three weeks of growth of the plant, PA treatment was beneficial to plant productivity, based on growth, even without added fertilizer. These results indicate that more efficient utilization of existing nutrients in the soil has occurred.

EXAMPLE 3

Effects of Polyaspartic Acid on Potassium Uptake in Early Sunglow Corn with No Added Fertilizer White corn (Early Sunglow; George W. Park Seed Co., Greenwood, S.C.) was grown in a greenhouse in one gallon pots filled with Fafard 3B potting soil. No fertilizer or potassium source were added to the pots. The pots were treated with varying dosages of polyaspartic acid (PA) of about 3,000–5,000 Mw, as in Example 2. After a 40 day growing period, the plants were harvested and potassium content of the plants was determined.

TABLE II

EFFECT OF POLYASPARTIC ACID ON POTASSIUM UPTAKE; EARLY SUNGLOW CORN; NO ADDED FERTILIZER; SINGLE TREATMENT/SOIL

| Dosage of Polyaspartic Acid Used | % Potassium In Corn Plants | % Increase of Potassium In Corn Plants |
| --- | --- | --- |
| 0 ppm | 2.6 | — |
| 1 ppm | 2.7 | 3.8 |
| 10 ppm | 3.0 | 15.4 |
| 100 ppm | 2.8 | 7.7 |
| 1000 ppm | 3.2 | 23.1 |

The data reported in Table II shows that a more efficient uptake of potassium by the corn plants resulted when PA was used without added fertilizer. At the 1,000 ppm dosage level, a 23.1% increase in potassium content was found in the corn plants.

EXAMPLE 4

Effect of Polyaspartic Acid on Phosphorous Uptake in Early Sunglow Corn with No Added Fertilizer White corn (Early Sunglow; George W. Park Seed Co., Greenwood, S.C.) was grown in a greenhouse in one gallon pots filled with Fafard 3B potting soil as in Examples 2 and 3. No fertilizer or phosphorus containing compounds were added to the pots. The pots were treated with varying dosages of polyaspartic acid (PA) (Mw 3,000–5,000) as in Examples 2 and 3. After a 40-day growing period, the plants were harvested and phosphorus content of the plants was determined. Results from this study are shown in Table III, below.

TABLE III

EFFECT OF POLYASPARTIC ACID ON PHOSPHORUS UPTAKE; EARLY SUNGLOW CORN; NO ADDED FERTILIZER; SINGLE TREATMENT/SOIL

| Dosage of Polyaspartic Acid Used | % Phosphorus In Corn Plants | % Increase of Phosphorus In Corn Plants |
| --- | --- | --- |
| 0 ppm | 0.3 | — |
| 1 ppm | 0.36 | 20.0 |
| 10 ppm | 0.34 | 13.3 |
| 100 ppm | 0.38 | 26.7 |
| 1000 ppm | 0.44 | 46.7 |

The results listed in Table III show that use of PA at all dosage levels tested increased phosphorus uptake by corn plants when no fertilizer was added. This indicates that a more efficient utilization of phosphorus sources existing in the soil has occurred. At the highest dosage level of PA, a 46.7% increase in phosphorus uptake by the corn plants was observed.

EXAMPLE 5

Effect of Polyaspartic Acid on Zinc Uptake in Early Sunglow Corn with No Added Fertilizer White corn (Early Sunglow) as was used in Examples 2, 3 and 4 was grown as before without added fertilizer. Again the same dosages of polyaspartic acid (PA) treatment for the corn plants was used as in Examples 2, 3 and 4. After a 40-day growing period, the plants were harvested and zinc content of the plants was determined. Results from this study are listed in Table IV, below.

TABLE IV

EFFECT OF POLYASPARTIC ACID ON ZINC UPTAKE; EARLY SUNGLOW CORN; NO ADDED FERTILIZER; SINGLE TREATMENT/SOIL

| Dosage of Polyaspartic Acid Used | Zinc In Corn Plants, ppm | % Increase of Zinc In Corn Plants |
| --- | --- | --- |
| 0 ppm | 29 | — |
| 1 ppm | 48 | 65.5 |
| 10 ppm | 45 | 55.2 |
| 100 ppm | 54 | 86.2 |
| 1000 ppm | 79 | 172 |

The above results from Table IV indicate that PA effectively increased the uptake of zinc in corn plants with no use of additional fertilizer. Even at a low dosage level of 1 ppm PA, a 65% increase in zinc uptake was observed. At a dosage of 1000 ppm of PA, a 172% increase in zinc uptake was found, further demonstrating the ability of PA to efficiently increase utilization of zinc in plant soil.

EXAMPLE 6

Effect of Polyaspartic Acid to Increase Plant Utilization of Limited Amounts of Nutrients Duckweed (*Lemna minor L.*) was grown in tap water containing as nutrient media a solution of Peters™ 20-20-20 fertilizer[1] (3 g/1.2 L) and a ¼-strength solution (750 mg/1.2 L) with and without 50 ppm by weight polyaspartic acid (PA). The nutrient media were adjusted to pH value of about 6.0. The Mw of the PA was about 3,000–5,000 (about 22 to about 40 repeating units).

[1] Total Nitrogen (N) 20%
3.90% Ammoniacal Nitrogen
6.15% Nitrate Nitrogen
9.95% Urea Nitrogen
Available Phosphoric Acid ($P_2O_5$) 20%
Soluble Potash ($K_2O$) . . . . . . . . . 20%
Derived from: Ammonium, Phosphate, Potassium Nitrate, Urea.
Commercially available from Grace-Sierra Horticultural Products Company, 1001 Yosemite Drive, Milpitas, Calif. 95035.

A single duckweed plant at the three-frond stage was placed in each flask. The flasks were then incubated under continuous light (500 lux) at 28°±2° C. for 21 days.

After 21 days, the plants were harvested, oven-dried, and weighed. Results show that nutrient reduction by 75% reduced plant weight by 74%, and that (a) no significant reduction in plant growth was found when PA was present in the medium with 25% nutrients indicating a more efficient use of a limited amount of nutrients and (b) plant growth was enhanced when PA was present in the medium with 100% nutrients. The results are presented in Table V, below. All reported values represent averages from 3 to 5 replicates.

TABLE V

RESULTS

Plant dry wt.—milligrams (mg)

| Treatment | Expt. A | Expt. B | Average | % Change |
| --- | --- | --- | --- | --- |
| 100% Nutrients | 16.5 | 17.7 | 16.6 | 0 |
| 100% Nutrients + PA | 21.3 | 22.2 | 21.7 | 31 |
| 25% Nutrients | 4.7 | 4.0 | 4.4 | −74 |
| 25% Nutrients + PA | 15.2 | 16.7 | 16.0 | 0 |

EXAMPLE 7

Effect of Polyaspartic Acid on Biomass

The procedure described in Example 6, above, was followed except that a chemically defined nutrient medium having the composition described in U.S. Pat. No. 4,813,997 to Kinnersley et al. (Nickell's medium with Fe present as $Fe^{2+}$ chelated with EDTA) was used. The plants were grown in five replicate flasks, harvested after 21 days, and the combined dry weight of the harvested plants was determined. The content of potassium and phosphorus in the plants and in the spent media was determined as well. The observed results are presented in Table VI, below.

TABLE VI

CHANGES IN BIOMASS

Amount of Mineral (µg) Control/With PA

| Treatment | Plant Biomass (mg) | Spent Media | Plants |
| --- | --- | --- | --- |
| 100% Nutrients/100% Nutrients + 50 ppm PA | 94.4/90.9 | | |
| Potassium (K) | | 11,610/11,740 | 1540/1530 |
| Phosphorus (P) | | 1170/1140 | 250/280 |
| 25% Nutrients/25% Nutrients + 50 ppm PA | 67.3/89.3 | | |
| Potassium (K) | | 2420/1170 | 990/1530 |
| Phosphorus (P) | | 334/322 | 125/173 |
| 12.5% Nutrients/12.5% Nutrients + 50 ppm PA | 54.1/62.7 | | |
| Potassium (K) | | 955/718 | 769/942 |
| Phosphorus (P) | | 190/192 | 89/111 |

The above results show that nutrient concentration reduced by 75% caused a 29% reduction in plant biomass (94.4–67.3) and a 36% reduction in the potassium content of plants (1540–990). However, in the same treatments containing polyaspartic acid the plant biomass was barely reduced (90.9–89.3), and the potassium content was unchanged. Analysis of the spent media showed much less potassium in the media containing PA. This data also indicates that the polymers had increased the uptake of potassium into plants.

The above results also show a remarkably good correlation between potassium content and plant-biomass as can be seen in Table VII, below.

TABLE VII

CORRELATION BETWEEN POTASSIUM CONTENT AND BIOMASS

| | Nutrients | | Nutrients + PA | |
|---|---|---|---|---|
| Nutrient Amount | Biomass (mg) | K (mg) | Biomass (mg) | K (mg) |
| 100% | 94.4 | 1.54 | 90.9 | 1.53 |
| 25% | 67.3 | 0.99 | 89.3 | 1.53 |
| 12.5% | 54.1 | 0.77 | 62.7 | 0.94 |

Potassium is the most important metal needed for plant growth, and is the principal metal component of most fertilizers. However, heretofore no agent was known able to simultaneously increase the growth and potassium content of plants.

EXAMPLE 8

Plant Content of Nutrients

The content of other nutrients in plants from the full strength and ¼-strength treatments described in Example 7, above, was determined. The observed results are set forth in Table VIII, below.

TABLE VIII

PLANT NUTRIENT CONTENT

Amount, micrograms (µg)

| Elements | 100% Nutrients | 25% Nutrients | 25% Nutrients + 50 ppm PA |
|---|---|---|---|
| Zn | 9.2 | 2.6 | 3.7 |
| Mg | 70 | 43 | 49 |
| Fe | 2.5 | 1.0 | 5.9 |
| Ca | 340 | 172 | 243 |
| Cu | 3.9 | 3.7 | 3.2 |
| Mn | 4.1 | 1.1 | 1.1 |
| Biomass, mg | 94.4 | 67.3 | 89.3 |

These results show that the content of most other minerals needed for plant growth was also greatly increased by the presence of PA. Particularly noteworthy is the substantial increase in the iron content at reduced nutrient level.

EXAMPLE 9

Effect of Polyaspartic Acid to Increase Plant Utilization of Limited Amounts of Nutrients Duckweed (*Lemna minor L.*) was grown in tap water under conditions described in Example 6, above, and containing as nutrient media a solution of Peters™ 20-20-20 fertilizer at full strength (100% nutrients), half strength (50% nutrients), and one-quarter strength (25% nutrients), with and without 50 ppm polyaspartic acid (PA) (Code DGI-KI) of about 3,000–5,000 Mw.

The plants were harvested, oven dried, and weighed after 21 days. The average plant dry weight is reported in Table IX, below. All reported values represent 12 to 20 replicates.

TABLE IX

RESULTS

| Treatment | Average Plant Dry Wt. milligrams (mg) |
|---|---|
| 100% Nutrients | 15.5 |
| 100% Nutrients + PA | 20.2 |
| 50% Nutrients | 8.8 |
| 50% Nutrients +PA | 15.1 |
| 25% Nutrients | 3.7 |
| 25% Nutrients + PA | 9.9 |

The foregoing results are depicted graphically in FIG. 5. These results show that the addition of PA permits decreasing the nutrient level by about 50% without a significant decrease in plant growth. From FIG. 5 it can also be seen that while the addition of PA to the nutrient solution increased plant growth at all nutrient levels, the effect of PA was much greater at the relatively lower levels of nutrients. Specifically, an increase in plant growth of about 168% was noted when PA was added to a 25% nutrient solution, and an increase of about 29% was noted when PA was added to a 200% nutrient solution. Therefore, when limited amounts of nutrients were available for plant growth, use of PA increased the efficiency of usage of these nutrients.

EXAMPLE 10

Effect of Polyaspartic Acid to Increase Bean Plant Utilization of Limited Amounts of Nutrients Garden beans (Mayo's Red Peanut Bush) were grown in the greenhouse in gallon pots filled with Fafard 3B potting soil. Ten pots were given 50 ml of a 7,500 ppm solution of Peters™ 20-20-20 nutrient. Twenty pots were given 50 ml of a 2,500 ppm Peters™ nutrient solution, and 10 of these pots were also given four weekly treatments of 50 ml aliquots of a 1 ppm solution of PA in water. When the bean plants flowered, they were taken outside for insect pollination. The beans that grew were harvested. The weight of beans on each plant was then determined. Results in Table X, below, show that PA increased reproductive growth results in a greater weight yield of beans from each plant. The increase in bean yield in the ⅓ fertilizer treatment with PA compared to the fertilizer alone, wa statistically significant with Duncan's multiple range test.

TABLE X

YIELD OF BEANS

| Treatment | Average Fresh Weight of Beans/Plant, g |
|---|---|
| 100% Nutrients | 6.4 |
| 33% Nutrients | 3.9 |
| 33% nutrients + 1 ppm PA | 7.2 |

The foregoing data show that when one-third the regular nutrient level was used along with 1 ppm of PA, the average fresh weight of bean/plant increased by 85%. This was a greater yield than was obtained when the 100% nutrient level was used. Under the conditions of limited nutrient availability, use of PA increased the efficiency of nutrient utilization resulting in increased bean yields.

EXAMPLE 11

Effect of Polyaspartic Acid to Increase Rapeseed Plant Utilization of Limited Amounts of Nutrients A fast growing variety of rapeseed (*Brasica rapus*) was obtained from the Crucifer Genetics Cooperative at the University of Wisconsin. This variety was grown in 9-cm pots in a greenhouse. Pots were given 50 ml of a full strength solution of Peters™ 20-20-20 nutrient (7,500 ppm) in water, or the same volume of a 3,750 ppm solution in water. Some of the pots were given 50 ml of a 2 or 20 ppm solution of polyaspartic acid (PA) in water as a single treatment. Plants were pollinated by hand when they flowered. Mature seed pods were harvested. The observed results are reported in Table XI, below.

TABLE XI

RAPESEED HARVEST

| Treatment | Average # Pods per Plant | Average Dry Weight of Pods per Plant, mg |
|---|---|---|
| Full Nutrient | 3.8 | 202 |
| 50% Nutrient | 2.9 | 174 |
| 50% Nutrient + 2 ppm PA | 4.8 | 283 |
| 50% Nutrient + 20 ppm PA | 5.2 | 290 |
| Full Nutrient + 2 ppm PA | 5.0 | 271 |

The above results show that average grain yield was higher in plants given PA than in plants receiving nutrient alone. PA increased grain yield in plants given both full and ½ strength nutrient. In many plants yield was higher for plants given ½ strength nutrient+2 ppm PA than in plants receiving full fertilizer alone. This result shows that use of PA increased the efficiency of utilization of a limited amount of nutrients available to the rapeseed plants.

EXAMPLE 12

Effect of Polyaspartic Acid on Duckweed Plants Grown in Tap Water

Duckweed was grown in tap water and in tap water solutions of polyaspartic acid (PA) following the procedure described in Example 6, above. Table XII, below, presents the compositions of the aqueous growth medium and the observed corresponding results. In each growth medium containing nutrients, the nutrient was Peters™ 20-20-20, and in each solution containing PA, the concentration of PA was 50 ppm.

TABLE XII

EFFECT OF POLYASPARTIC ACID ON DUCKWEED PLANTS GROWN IN TAP WATER

| | Aqueous Growth Medium | Plant Dry Wt. (mg) | % Change |
|---|---|---|---|
| A. | Nutrient (2.2 g/L) | 37 | |
| | Nutrient (2.2 g/L) + PA | 78 | 111 |
| B. | Nutrient (1.1 g/L) | 18 | |
| | Nutrient (1.1 g/L) + PA | 57 | 217 |
| C. | Nutrient (0.55 g/L) | 17 | |
| | Nutrient (0.55 g/L) + PA | 22 | 72 |
| D. | Tap water only[1] | 20 | |
| | Tap water + PA | 26 | 30 |

[1]There is some mineral content in tap water.

In the above table, each treatment dosage of nutrient combined with PA is compared to the same nutrient dosage without PA (the control) and % change in plant weight compared to the corresponding control is given. The above results show that PA was least effective at promoting plant growth when it was given with treatment D that has no added nutrients. If, in fact, PA was acting as a fertilizer, it should have been most effective (as measured by relative % change over control) when plants had no added nutrient for growth. Actually, the reverse was observed to be true. PA was only effective in promoting plant growth in conjunction with a real nutrient source. In treatment D, when no nutrient was added, use of PA still permitted increased plant growth by facilitating uptake of minerals from the tap water.

EXAMPLE 13

Effect of Polyaspartic Acid on Duckweed Plants Grown in Deionized Water

Duckweed was grown in deionized water and in deionized water solution of polyaspartic acid (PA) following the procedure described in Example 6, above, except that the plants were harvested after four weeks instead of 21 days. Table XIII, below, presents the composition of the aqueous growth media that was used and the corresponding observed results. Because the biomass of each plant was so minimal, plants from eight replicate flasks of each treatment were combined to provide enough plant material to be weighed accurately.

TABLE XIII

EFFECT OF POLYASPARTIC ACID ON DUCKWEED PLANTS GROWN IN DEIONIZED WATER

| | Aqueous Growth Medium | Plant Dry Wt. (mg) | % Change |
|---|---|---|---|
| A. | Deionized water | 8 | |
| B. | Deionized water + PA (50 ppm) | 2 | −75 |

The above results show that PA did not increase plant growth when added to deionized water from which all minerals had been removed. This effect would not have been observed if PA was functioning as a fertilizer.

The tests performed with duckweed plants as described in Examples 12 and 13, above, demonstrate (a) that PA had minimal biological activity when supplied to plants grown in tap water and (b) that PA itself showed no nutrient or fertilizer activity with regard to these plants when the plants were grown in deionized water.

In U.S. Pat. No. 4,839,461 to Boehmke it is stated that K, Mg, and Ca salts of polyaspartic acid are suitable for use as fertilizers. No experimental evidence or examples are given to support this statement. The above tests with Duckweed plant in tap water and deionized water show that PA itself does not act as a fertilizer. It is likely that if the Ca, K and Mg salts of PA act as fertilizers, this activity is due to the nutrient value of Ca, K and Mg ions themselves rather than PA.

EXAMPLE 14

Effect of Polyaspartic Acid on Corn Plants

White corn (*Zea mays L.*) seed (5145 Truckers Favorite; George W. Park Seed Co., Greenwood, S.C.) was planted in 8-cm black round pots with Fafard 3B potting soil. Each pot was given 0.3 g, 0.15 g, or 0.075 g of Peters™ 20-20-20 nutrient. Five pots representing each treatment were kept as controls, five pots were given 50 ml of 5 ppm aqueous polyaspartic acid (PA) solution, and five pots 50 ml of a 500 ppm aqueous PA solution. After six weeks the plants were harvested, and the fresh weight and nitrogen content of the harvested plants was determined. The observed results are reported in Table XIV, below.

TABLE XIV

EFFECT OF POLYASPARTIC ACID ON CORN PLANTS

| Treatment | Fresh wt., g | Average N Content, mg |
|---|---|---|
| 100% Nutrients | 45.8 | 67.6 |
| 100% Nutrients + 5 ppm PA | 46.5 | 75.7 |
| 100% Nutrients + 500 ppm PA | 50.2 | 73.2 |
| 50% Nutrients | 34.7 | 40.5 |
| 50% Nutrients + 5 ppm PA | 45.6 | 57.6 |
| 50% Nutrients + 500 ppm PA | 38.6 | 49.6 |
| 25% Nutrients | 24.1 | 29.6 |
| 25% Nutrients + 5 ppm PA | 31.7 | 36.2 |
| 25% Nutrients + 500 ppm PA | 38.3 | 47.8 |

Above results show that PA enables plants to be grown with a 50% reduction in nutrients without showing any reduction in growth. Simultaneously with increasing the corn biomass, PA also increased the nitrogen content of the corn. Plants grown with 25% nutrients and 500 ppm PA contained more nitrogen than plants grown with 50% nutrients that were given twice the amount of nitrogen.

EXAMPLE 15

Environmental Stability of Polyaspartic Acid

A nutrient solution was made by adding Peters™ 20-20-20 nutrient (375 mg) to tap water (150 ml). The solution was divided into three aliquots. One 50-ml aliquot was maintained as a control. To another aliquot was added 1,000 ppm of polyaspartic acid, and 1000 ppm of lactic acid oligomer containing less than ten lactic acid residues and obtained by thermal condensation of 88% L-lactic acid by heating at 70° C. for 4 hours followed by heating under vacuum at 100° C. for 4 hours was added to the last 50-ml aliquot.

The turbidity of the samples were measured every day to ascertain the extent of microbial growth in each sample. Within a few days the solution containing the lactic acid oligomer had become milky, indicating microbial contamination. The sample containing polyaspartic acid remained substantially clear, even after 7 days. The observations are compiled in Table XV, below.

TABLE XV

TURBIDITY MEASUREMENTS

| | DAYS | | | | |
|---|---|---|---|---|---|
| | 1 | 2 | 3 | 4 | 5 |
| Control | 0 | 0 | 0 | 0 | 0 |
| Polyaspartic Acid | −0.04 | +0.25 | +0.26 | +0.40 | +0.95 |
| Lactic Acid Oligomer | −0.11 | +2.20 | +3.45 | +16.5 | +382.0 |

Results indicate that polyaspartic acid has a relatively longer life in the environment.

EXAMPLE 16

Nutrient Composition for Hydroponic Growing

An illustrative aqueous composition suitable for incorporating polyamino acid or a crosslinked polyamino acid embodying the present invention and well suited for hydroponic farming is set forth in Table XVI, below.

TABLE XVI

HYDROPONIC GROWING MEDIUM

| Nutrients | ppm by weight |
|---|---|
| Nitrogen as N | 50 |
| Phosphorus as P | 48 |
| Potassium as K | 210 |
| Magnesium as Mg | 30 |
| Sulfates as $SO_4^{-2}$ | 117 |
| Sodium as Na | 3.619 |
| Chlorides as Cl | 0.04 |
| Iron as Fe | 3 |
| Zinc as Zn | 0.15 |
| Copper as Cu | 0.15 |
| Boron as B | 0.5 |
| Manganese as Mn | 0.5 |
| Molybdenum as Mo | 0.1 |
| Water, q.s. | |

EXAMPLE 17

Stress Protection and Enhanced Plant Productivity by Crosslinked Polyaspartic Acid Duckweed (*Lemna minor L.*) was grown in an aqueous solution containing relatively low levels of nutrients as shown in the following Table XVII.

TABLE XVII

LOW NUTRIENT COMPOSITION

| Nutrient Element | Concentration (ppm as element) |
|---|---|
| Nitrogen (N) | 12.5 |
| Phosphorus (P) | 3 |
| Potassium (K) | 12 |
| Calcium (Ca) | 10 |
| Magnesium (Mg) | 4 |
| Sulfur (S) | 14 |
| Iron (Fe) | 1 |
| Water, q.s. | |

Tests were performed in which the plants were grown in separate flasks under controlled conditions employing the low nutrient solution which was enhanced by the addition of 50 ppm by weight of a selected crosslinked polyaspartate, identified as Compound A or B in Table XVIII, below. Compound A represents a polyaspartate in which the crosslinked polyamino acid is crosslinked with an organic divalent base and Compound B represents a polyaspartate in which the crosslinked polyamino acid is crosslinked by free radical technique with hypophosphite.

TABLE XVIII

POLYASPARTATE COMPOUND

A. sodium salt of polyaspartic acid, crosslinked with 10 mol % meta-xylylenediamine (Mw about 80,000)
B. 80 mol % aspartic acid/20 mol % N-allylaspartamide copolymer, free radical crosslinked with hypophosphite, sodium salt (Mw about 53,311)

For evaluating stress protection, a similar series of tests were performed in which the plants were grown employing each of the foregoing compositions to which 3 ppm of $Cu^{++}$ ion was also added. For each test, the enhanced nutrient solution was adjusted to pH 6.7±0.1 and five replications were performed for each compound tested, both with and without the added copper.

A single duckweed plant at the three-frond stage was placed in each of five flasks. The flasks were then incubated under continuous light (natural light supplemented by metal halide lights; photon flux density 500 micromoles per $m^2$ per sec.) in a greenhouse at a temperature of about 28°±2° C. for three days. The plants were then harvested after three days, oven dried to constant weight at 80° C. and weighed. The average plant dry weight per replicate is reported in Table XVIX, below. All reported values represent the averaged weight of the five replicates.

TABLE XVIX

STRESS PROTECTION AND PLANT PRODUCTIVITY

AVERAGE BIOMASS (mg)

| Compound | No $Cu^{++}$ | % Imp.* | 3 ppm $Cu^{++}$ | % Imp.* |
|---|---|---|---|---|
| None (Control) | 9.648 | | 3.338 | |
| A | 11.03 | 14 | 4.646 | 39 |
| B | 11.6 | 20 | 4.872 | 46 |

*% Improvement shows increase in average biomass weight when crosslinked polyaspartate is present over that of the control.

The data show that the addition of either one of the crosslinked polyaspartates to the low level nutrient solution resulted in enhanced plant productivity based on an average biomass increase of more than 10%. The data also show that the stressing effect of copper toxicity decreased the biomass of the control by 65%. In contrast the presence of either one of the crosslinked polyaspartates afforded a degree of stress protection by reducing the limiting effect of the copper toxicity to about 57–58%. Thus, the crosslinked polyaspartate enhanced plant productivity by more than one-third.

The foregoing specification and the Examples are intended to illustrate the present invention, but are not to be taken as limiting.

We claim:

1. A method for enhancing plant productivity by supplying to the plant a composition containing a productivity enhancing amount of a crosslinked polyamino acid characterized by being water soluble and having a weight average molecular weight larger than about 1,500.

2. The method of claim 1 wherein the composition supplied is in the form of an aqueous liquid.

3. The method of claim 1 wherein the composition supplied is in a substantially solid form.

4. The method of claim 1 wherein the crosslinked polyamino acid is supplied separately or in combination with a fertilizer.

5. The method of claim 1 wherein the composition supplied contains a water-soluble, non-peptidal polymer.

6. The method of claim 1 wherein the crosslinked polyamino acid is derived from a crosslinkable polyamino acid or salt thereof selected from the group consisting of polyaspartic acid, polyglutamic acid, polylysine, polyglycine, polycysteine, polyserine, block copolymers thereof, random copolymers thereof, terpolymers thereof, and mixtures thereof.

7. The method of claim 1 wherein the crosslinked polyamino acid is crosslinked polyaspartic acid or salt thereof.

8. The method of claim 7, wherein the crosslinked polyaspartic acid has a weight average molecular weight of at least about 2,000.

9. The method of claim 1, wherein the crosslinked polyamino acid is derived from polyaspartic acid having aspartic acid residues of at least 20% of the total number of residues in the polymer.

10. The method of claim 1 wherein the composition supplies crosslinked polyamino acid in an amount of 10 parts per billion by weight.

11. The method of claim 1 wherein the crosslinked polyamino acid is derived from a crosslinked polysuccinimide.

12. The method of claim 1 wherein a crosslinked precursor of a polyamino acid is supplied to the plant and hydrolyzed in situ.

13. The method of claim 1 wherein the crosslinked polyamino acid is crosslinked with an organic base.

14. The method of claim 13 wherein the crosslinked polyamino acid is polyaspartic acid crosslinked with meta-xylylenediamine.

15. The method of claim 14 wherein the crosslinked polyamino acid is a salt of polyaspartic acid crosslinked with 10 mol % meta-xylylenediamine and has a weight average molecular weight of about 80,000.

16. The method of claim 1 wherein the crosslinked polyamino acid is free radical crosslinked.

17. The method of claim 16 wherein the crosslinked polyamino acid is free radical crosslinked with hypophosphite.

18. The method of claim 17 wherein the crosslinked polyamino acid is a salt of a copolymer of 80 mol % aspartic acid/20 mol % N-allylaspartamide copolymer and has a weight average molecular weight of about 53,311.

19. A method for enhancing plant productivity by supplying to the plant a composition containing a productivity enhancing amount of a crosslinked polysuccinimide.

20. An improved composition for enhancing plant productivity containing a fertilizer together with a productivity enhancing amount of a crosslinked polyamino acid which is water soluble and has a weight average molecular weight larger than about 1,500.

21. The composition of claim 20 wherein the crosslinked polyamino acid is derived from a polyamino acid selected from the group consisting of polyaspartic acid, polyglutamic acid, polylysine, polyglycine, polycysteine, polyserine, block copolymers thereof, random copolymers thereof, terpolymers thereof and mixtures thereof.

22. The composition of claim 20 wherein the crosslinked polyamino acid is present in an amount of at least about 10 parts per billion by weight of the composition.

23. The composition of claim 20 wherein the crosslinked polyamino acid is crosslinked polyaspartic acid or salt thereof.

24. The composition of claim 20 wherein the crosslinked polyamino acid is derived from hydrolyzable crosslinked polysuccinimide.

25. The composition of claim 20 wherein the crosslinked polyamino acid is crosslinked with an organic base.

26. The composition of claim 20 wherein the crosslinked polyamino acid is polyaspartic acid crosslinked with meta-xylylenediamine.

27. The composition of claim 20 wherein the crosslinked polyamino acid is a salt of polyaspartic acid crosslinked with 10 mol % meta-xylylenediamine and has a weight average molecular weight of about 80,000.

28. The composition of claim 20 wherein the crosslinked polyamino acid is free radical crosslinked.

29. The composition of claim 20 wherein the crosslinked polyamino acid is free radical crosslinked with hypophosphite.

30. The composition of claim 20 wherein the crosslinked polyamino acid is a salt of a copolymer of 80 mol % aspartic acid/20 mol % N-allylaspartamide copolymer and has a weight average molecular weight of about 53,311.

31. The composition of claim 20 including a water-soluble, non-peptidal polymer.

32. The composition of claim 20 in the form of an aqueous liquid.

33. The composition of claim 20 in the form of a solid.

* * * * *